US009688781B2

(12) United States Patent
Meyer et al.

(10) Patent No.: US 9,688,781 B2
(45) Date of Patent: *Jun. 27, 2017

(54) SUPERABSORBENT POLYMER COMPOSITE PARTICLES AND PROCESSES THEREFORE

(75) Inventors: Axel Meyer, Frankfurt/M (DE); Torsten Lindner, Kronberg/Ts (DE); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 631 days.

This patent is subject to a terminal disclaimer.

(21) Appl. No.: 12/838,862

(22) Filed: Jul. 19, 2010

(65) Prior Publication Data

US 2011/0015296 A1 Jan. 20, 2011

(30) Foreign Application Priority Data

Jul. 20, 2009 (EP) ..................................... 09165870
Jul. 8, 2010 (WO) ................ PCT/US2010/041337

(51) Int. Cl.
*C08F 8/42* (2006.01)
*C08F 2/46* (2006.01)
*C08F 2/44* (2006.01)
*A61L 15/60* (2006.01)
*C08F 8/00* (2006.01)

(52) U.S. Cl.
CPC ................ *C08F 2/44* (2013.01); *A61L 15/60* (2013.01); *C08F 8/00* (2013.01)

(58) Field of Classification Search
CPC ...... A61L 15/60; A61L 15/18; A61L 26/0004; A61L 15/22; A61L 2400/12; A61L 15/24; A61L 2/18; A61L 2/208; C08F 220/06; C08F 292/00; C08L 101/14; C08L 2207/53; C08L 33/04; C08L 2205/18

USPC .......... 264/9, 5, 13; 435/176, 177, 180, 396; 522/182, 160; 525/330.2
See application file for complete search history.

(56) References Cited

U.S. PATENT DOCUMENTS

| 5,269,980 | A | * | 12/1993 | Levendis et al. ............... 264/9 |
| 6,610,780 | B1 | * | 8/2003 | Payzant .................. A61L 15/18 524/445 |
| 7,993,892 | B2 | * | 8/2011 | Takada et al. ................ 435/176 |
| 2005/0239942 | A1 | * | 10/2005 | Herfert et al. ................ 524/445 |
| 2009/0192035 | A1 | * | 7/2009 | Stueven et al. ............... 502/402 |
| 2009/0291500 | A1 | | 11/2009 | Takada et al. |
| 2010/0057027 | A1 | | 3/2010 | Furno et al. |
| 2010/0210746 | A1 | * | 8/2010 | Gustafson ............... A61L 15/18 521/149 |

FOREIGN PATENT DOCUMENTS

WO    WO-2009/109563    9/2009

OTHER PUBLICATIONS

"Effects of clay content on the properties of nanocomposite hydrogels composed of poly(n-isopropylacrylamide) and clay" Haraguchi et al. Macromolecules, 35, 10162-10171, 2002.*
PCT International Search Report, PCT/2010/041337 date of mailing Jul. 9, 2010.

* cited by examiner

*Primary Examiner* — Jeffrey Washville
(74) *Attorney, Agent, or Firm* — Kathleen Y. Carter

(57) ABSTRACT

Superabsorbent material, comprising clay-crosslinked superabsorbent polymers, obtainable by polymerizing in a spray-stream, polymerizable compounds in the presence of a polymerization initiator system, and nano-sized or individual clay particles, which are all introduced into a vessel by a spraying step in the form of a said spray-stream thereof, whereby said clay particles crosslink said polymers during polymerization. The invention also relates to such a process and absorbent articles comprising such superabsorbent material.

25 Claims, No Drawings

SUPERABSORBENT POLYMER COMPOSITE PARTICLES AND PROCESSES THEREFORE

FIELD OF THE INVENTION

The present invention relates to a superabsorbent material, comprising clay-crosslinked superabsorbent polymers, obtainable by polymerizing in a spray-stream, polymerizable compounds in the presence of a polymerization initiator system, and nano-sized or individual clay particles, which are all introduced into a vessel by a spraying step in the form of a said spray-stream thereof, and whereby said clay particles crosslink said polymers during polymerization, forming individual clay particle crosslinks and/or nano-size clay crosslinks, as defined herein. The invention also relates to such a process and absorbent articles comprising such superabsorbent material.

BACKGROUND TO THE INVENTION

Disposable absorbent articles (such as diapers) include typically an absorbent core structure with superabsorbent polymers, typically hydrogel-forming water-swellable polymers (also referred to as absorbent gelling material, AGM, or superabsorbent polymers, SAP's). This polymer material ensures that in use, large amounts of bodily fluids, e.g. urine, can be absorbed by the article and locked away, thus providing low rewet and good skin dryness.

These water-swellable or superabsorbent polymers need to have adequately high sorption capacity, as well as adequately high gel strength. Sorption capacity needs to be sufficiently high to enable the absorbent polymer to absorb significant amounts of the aqueous body fluids encountered during use of the absorbent article. Together with other properties of the gel, gel strength relates to the tendency of the swollen polymer particles (i.e. gel) to resist deformation under an applied stress in the absorbent article. The gel strength needs to be high enough in the absorbent article so that the particles do not deform too much and thereby fill the capillary void spaces to an unacceptable degree, which would cause so-called gel blocking. This gel-blocking inhibits the rate of fluid uptake and/or the fluid distribution: i.e. once gel-blocking occurs, it can substantially impede the distribution of fluids to relatively dry zones or regions in the absorbent article; then, leakage from the absorbent article can take place well before the superabsorbent polymer particles are fully saturated or before the fluid can diffuse or wick past the "blocking" particles into the rest of the absorbent article. Thus, it is important that the superabsorbent polymers (when incorporated in an absorbent structure or article) maintain a high wet-porosity and have a high resistance against deformation thus yielding high permeability for fluid transport through the swollen gel bed.

Absorbent polymers with relatively high permeability can be made by increasing the level of internal crosslinking or surface crosslinking, which increases the resistance of the swollen gel against deformation by an external pressure (such as the pressure caused by the wearer), but these techniques typically also reduce the absorbent capacity of the gel undesirably.

In addition, there is also a need for superabsorbent polymer particles that have a greater speed of absorption. It has been found that the prior art superabsorbent polymers that may have high gel strength, may often not have a high absorption speed.

In recent years, some absorbent polymers that are crosslinked by nano-sized clay particles have been proposed. Unlike some superabsorbent material whereby clay is added after polymerization, it has been found to be important that the clay is added in nano-size prior to polymerization, to ensure the clay form strong crosslinks between the polymers. This is for example described in "Nanocomposite Polymer Gels"; Schexnailder/Schmidt; *Coloid Polym Sci* (2009) 287: 1-11. Some of said clay-crosslinked polymers form elastic or stretchable hydrogels upon swelling. For example, water-containing hydrogel shaped or molded articles, comprising certain specific isopropyl polyamides cross-linked by certain clay particles are described in *Macromolecules* 2002, 35, 10162-10171 (Kazutoshi Haraguchi et all); these elastic, shaped hydrogels are intended for medical purposes where they can be used in applications where they can de-water quickly, and thus shrink, upon demand, e.g. driven by temperature changes. WO09/041870 and WO2009/041903 describe the desire to make clay-linked polyacrylates, which provide a better absorbency, but that polyacrylates cannot be linked by nano-size clay particles successfully, because the clay agglomerates in the presence of acrylate or acrylic acid. They teach thereto fibers, foams and gels (that may be made in particles) of clay-linked hydrogels, made by mixing nano-size clay particles and acrylic esters in a liquid to form clay-linked polyacrylic esters, that may be shaped in foams, fibers, gels etc. These polyacrylic ester shapes are then hydrolyzed using conventional hydrolysis techniques in order to obtain polyacrylate shapes (e.g. foams, fibers, gels, etc.). However, the hydrolyses of complete foams, fibers or gels, or even batches of finished particles of polyacrylic esters is a very slow and energy-demanding process, because the penetration of the hydrolysis solution is driven by diffusion only which is a generally slow process, in particular if larger shapes such as foams or gels need to be hydrolyzed (internally).

Furthermore, hydrolysis of ground particles would cause the particles to form a gel blocks (the particles would stick together due to the hydrolysis solvent liquid), which would then need to be dried and grinded, sieved etc. to obtain particles. Thus, with the above described processes, this process would need to be done twice.

In addition, it is difficult to achieve a very homogeneous hydrolysis throughout the entire polymer particles, i.e. some parts of the polymer may be hydrolyzed earlier and to a larger extent than others. Furthermore, by-products from the hydrolysis (such as methanol or ethanol) would need to be removed from the product, and the level of these by-products would need to be brought to very low levels (toxicity, odour).

Thus, the proposed clay-crosslinked polyester gel blocks and foams, or even fibers or particles, and the hydrolysis thereof are not suitable for commercial scale production of clay-linked polyacrylates (particles). The present invention provides processes whereby said hydrolysis can be avoided, or if necessary, can be done in an effective manner.

SUMMARY OF THE INVENTION

In order to provide a solution to the problems above, there is disclosed a superabsorbent material, comprising clay-crosslinked superabsorbent polymers, obtainable by the process of,
  a) providing a dispersion or solution of polymerizable compounds in carrier liquid, and a dispersion of clay particles in a carrier liquid; and providing a polymerization initiator (system), preferably as a dispersion or solution in a carrier liquid;

b) introducing said dispersions/solutions and initiator of step a) into a spraying tool and spraying said dispersions/solutions and initiator into a vessel to obtain a spray-stream thereof and optionally activating said initiator, starting (thereby) polymerization of said polymerizable compounds and crosslinking thereof by said clay particle, e.g. partially or substantially completely exfoliated and/or individual clay particles/platelets;

c) optionally spraying further components into said vessel;

d) removing at least part of said carrier fluid, to obtain clay-crosslinked superabsorbent polymers in solid or gel form, whereby said clay particles have a weight average largest particle dimension of less than 800 nm and/or are substantially individual clay particles;

e) optionally, post-treating of the resulting particles of step d).

The invention also relates to said process as defined above.

The invention also relates to superabsorbent material, comprising clay-crosslinked superabsorbent polymer particles, obtainable by polymerizing polymerizable compounds in the presence of clay particles and a polymerization initiator, whereby said clay particles have a have a weight average largest particle dimension of less than 800 nm and/or are substantially individual clay particles; and whereby said spraying step b) involves spraying the dispersions/solutions and initiator in the form of: i) a multitude of droplets into a gas-containing vessel, or ii) a multitude of spray-streams into a gas-containing vessel, said streams being then dispersed into droplets; and whereby said clay-crosslinked superabsorbent polymer particles have a core enclosing an internal void volume.

In the present process, step a) can be done such that the clay dispersion and the polymerizable compound solution or dispersion, and optionally the initiator system, (preferably dispersion or solution thereof) are combined only upon introduction into step b) or just prior to (e.g. less than 30 seconds, preferably less than 10 seconds, or less than 5 seconds, or less than 2 seconds) step b)—the spraying step—e.g. just prior to or upon introduction thereof into a spray tool, (e.g. into one or more inlets thereof). Thus, the mixing of said clay dispersion and polymerizable compound dispersion/solution can be done in the spraying step/tool, to avoid extended exposure of said clay dispersion to said polymerizable compounds. Thereby, aggregation of the clay particles can be reduced or avoided and it can be ensured that dispersed clay of the specified particle size above, or preferably exfoliated clay, being in the form of individual clay particles, is present during polymerization (that is initiated during to spraying step or upon entry into the vessel). Thus, said dispersed nano-sized clay particles or individual clay particles/platelets can crosslink the polymers that are being formed in the spray-stream in the vessel. Thus, a uniform clay distribution in the formed clay-crosslinked superabsorbent polymers is achievable, and said clay particles therein are of nano-size, as specified above or they are individual clay particles (platelets). It should be noted that once said spray-stream has reached a certain degree of polymerization, the clay particles therein are immobilized and no further aggregation is possible.

In one embodiment herein, said spraying step involves the formation of one or more spray-streams that are formed into droplets, and the polymerization and clay-crosslinking takes place in the droplets; said droplets are subsequently dried to remove the carrier liquid to form particles.

The resulting clay-crosslinked superabsorbent polymers, e.g. particles, may have a very uniform chemistry, composition and/or particle sizes, and hence uniform properties.

In one embodiment herein, said polymerizable compounds have a charged group precursor group, and said resulting polymers have a charged group precursor group, as defined herein, that is subsequently hydrolysed. This is in particular useful for clay-crosslinked superabsorbent polymers that are in the form of particles that enclose an internal void volume, e.g. with a shell make of said clay-crosslinked superabsorbent polymers and a core enclosing a void volume; said shell being more readily hydrolysable. This is believed to be due to the fact that hydrolysis of particles is driven by the diffusion speed of the hydrolysis solution into the particle; said void particles have a larger surface area per mass and hydrolysis can be done faster (per mass), and thus in a more effective manner.

However, in one embodiment herein, hydrolysis is avoided, and the polymerizable compounds comprise or consist of polymerizable compounds with a cationic or anionic charged group, preferably an anionic charged group, which includes, as set out herein, acids forms of such anionic groups, and/or base forms of such cationic groups.

As described herein, said clay-crosslinked superabsorbent polymers are typically made in a manner whereby said partly or substantially completely exfoliated clay dispersion and said dispersion/solution of said polymerizable compound are only combined at the spraying step or just before said spraying step, and said polymerization is only started at the spraying step or just before the spraying step, and said the polymerization commences immediately upon initiation throughout the spray-stream/droplets. Because of this, the spray-stream (or: droplets) comprise almost immediately after initiation polymerizing polymers that are already in gel-form; then, very limited or no aggregation can occur (the clay is "immobilized"). Thus, this allows the use of polymerizable compounds that have a cationic or anionic group, without causing significant aggregation.

Furthermore, said spraying step may apply a high shear force to said dispersion(s)/solution(s). Hence, even a non-homogeneous dispersion, or a partially exfoliated clay dispersion can be used herein, because said spraying process step may apply such a high shear force that said clay dispersion is made into a homogeneous and/or a substantially exfoliated (preferably completely exfoliated) clay dispersion.

DETAILED DESCRIPTION

"Superabsorbent material" and "superabsorbent polymers" or "superabsorbent polymer particles" as used herein, refers to a material, or to polymers or particles that absorbs and retains at least 10 grams of saline (0.9% saline solution in de-mineralized water), per gram of superabsorbent material, or polymers or particles, as measurable by the CRC method, described in detail below.

The superabsorbent material, and the superabsorbent polymers and superabsorbent polymer particles herein are water-swellable. That is the superabsorbent material will swell in a 0.9% saline solution in demineralised water, by absorbing the said saline water; they may thereby form a gel. The superabsorbent material herein may comprise other components that are not said clay-crosslinked superabsorbent polymers. However, the clay-crosslinked superabsorbent polymers (particles) herein are present at a level of. e.g., at least 20% by weight (of the superabsorbent material from 50% to 100% by weight or even from 80% to 100% by weight, and even between 90% and 100% by weight of said superabsorbent material.

The clay-crosslinked superabsorbent polymers and said superabsorbent material are in solid form, and typically in the form of a gel, film, or foam, or in one embodiment herein, in particulate form, which includes for the purpose of the invention flakes, fibers, agglomerates, blocks, granules, particles, spheres. The superabsorbent material and/or the clay-crosslinked superabsorbent polymers herein are in the form of particles having a mass median particle size up to 2 mm, or even between 50 microns and 2 mm or to 1 mm, or between 100 μm and 800 μm, as can for example be measured by the method set out in for example EP-A-0691133.

In one embodiment of the invention the superabsorbent material and/or the superabsorbent polymer particles of the invention are in the form of ("free" flowing) particles with particle sizes between 10 μm and 1200 μm or even between 50 μm and 800 μm and a mass median particle size between 100 or 200 and 800 μm or 600 μm.

In addition, or in another embodiment of the invention, said particles are essentially spherical.

In yet another or additional embodiment of the invention the superabsorbent material and/or clay-cross-linked superabsorbent polymer particles of the invention have a relatively narrow range of particle sizes, e.g. with the majority (e.g. at least 80% or preferably at least 90% or even at least 95%) of particles having a particle size between 50 μm and 800 μm, between 100 μm and 600 μm, or even between 200 μm and 600 μm.

The superabsorbent material and/or superabsorbent polymer (particles) of the invention preferably comprise less than 15% by weight of water, or less than 10%, or less than 8% or less than 5%, or no water. The water-content can be determined by the Edana test, number ERT 430.1-99 (February 1999) which involves drying the superabsorbent material at 105° Celsius for 3 hours and determining the moisture content by the weight loss of the superabsorbent materials after drying.

Suitable superabsorbent materials and/or clay-crosslinked superabsorbent polymers herein have a high sorption capacity measured by the commonly used Centrifugation Retention Capacity test, CRC, (as described below); said CRC being at least 10 g/g, 20 g/g, or even at least 30 g/g. Upper limits may be up to 150 g/g, or up to 100 g/g/or up to 80 g/g.

Suitable superabsorbent materials and/or clay-crosslinked superabsorbent polymers herein have a good permeability for liquid, for example, exhibiting an SFC value of at least $10 \times 10^{-7}$ cm$^3$ s/g; at least $30 \times 10^{-7}$ cm$^3$·s/g, at least $50 \times 10^{-7}$ cm$^3$/s/g $10 \times 10^{-7}$ cm$^3$s/g, or at least $100 \times 10^{-7}$ cm$^3$s/g, or even at least $120 \times 10^{-7}$ cm$^3$sec/g. This SFC is a measure of permeability and an indication of porosity is provided by the saline flow conductivity of the gel bed as described in U.S. Pat. No. 5,562,646, (Goldman et al.) issued Oct. 8, 1996 (whereby however a 0.9% NaCl solution is used instead of Jayco solution). Upper limits may for example be up to 350 or up to 250 ($\times 10^{-7}$ cm$^3$·s/g).

The superabsorbent material of the invention may be used in an absorbent structure, together with (mixed with) other materials, such as fibers, (fibrous) glues, organic or inorganic filler materials or flowing aids, process aids, anticaking agents, odor control agents, colouring agents, coatings to impart wet stickiness, hydrophilic surface coatings, other superabsorbent polymer particles, not comprising clay-crosslinked, etc. This is described in more detail below.

The clay-crosslinked superabsorbent polymers herein are formed by polymerizing polymerizable compounds (e.g. monomers) in the presence of clay particles, specified below, so that said clay particles crosslink said polymers. It is thus essential that said clay particles are present during the polymerisation of said polymerizable compounds.

The polymerizable compounds may comprise repeating units of monomer groups, for example the polymerizable unit may be a di-mer. However, in certain embodiment, the polymerizable compounds are monomers.

The polymerizable compounds may be in the form of a dispersion or typically a solution, and as such introduced into the spraying step; said clay particles are typically in the form of a dispersion. Any combination herein of: a dispersion or solution in a carrier liquid of polymerizable compounds and separately, a dispersion of clay particles in a carrier liquid, or mixture of thereof, is herein referred to as "dispersion/solution".

The polymerizable compounds, e.g. monomers, are used herein as a solution or dispersion thereof in a carrier liquid at any level as known in the art, for example, at least 1% by weight, and typically up to 90% by weight, or for example from 10% to 60% by weight based on the weight of the solution.

The carrier liquid may be an aqueous liquid such as, for example, water.

Without wishing to be bound by theory, it is believed that superabsorbent polymers crosslinked via said nano-sized clay particles have a narrower distribution of the length of the polymer chain segments between two cross-linking points (e.g. two clay particles). It is thus believed that said polymer chain segments are of similar chain length and that they are hence able to (substantially) all move and expand to a similar extent when the superabsorbent polymer particles swell due to fluid-absorption. It is believed that, mechanistically, the polymers connected to the same clay particle sustain a force (stretching or pressure) cooperatively; this then can increase the elongation to break compared to traditional crosslinked polymer networks, whereby the crosslinking is achieved by organic crosslinking groups. This is believed to reduce deformation and hence reduce gel blocking. Furthermore, it is believed that due to the hydrophilic nature of the clay particles, the resulting superabsorbent polymers can have an advantage in the absorption speed.

In general, it is believed that polyelectrolyte polymers provide the required osmotic pressure that drives the required absorption and retention of fluids like urine. Thus, in order to further increase the capacity of the clay-crosslinked superabsorbent polymers and superabsorbent material herein, the superabsorbent polyelectrolyte polymers may be polyelectrolytes, and may be anionic. Thus, in one embodiment, the resulting clay-crosslinked superabsorbent polymers are superabsorbent polyelectrolyte polymers that are cross-linked by said clay particles.

Thus, in certain embodiments, the clay-crosslinked superabsorbent polymers are, for example, made by polymerizing polymerizible compounds, e.g. monomers, which have a charged group, or precursor group thereof, an anionic group or a precursor thereof, or a mixture of compounds (monomers) with a cationic group or precursor thereof, and compounds (monomers) with an anionic group or precursor thereof. (Such groups extend from the polymer backbone).

It should be understood that for the purpose of the invention that a group that has an acid and base form, such as a carboxylic acid group, is herein considered a charged group, since it would in the dispersion/solution used herein be at least partially in its charged form, e.g. carboxylate form.

In certain embodiments, the polymerizable compounds have cationic group- and/or anionic group-precursor groups, said precursor groups being neutral. Said anionic or cationic group precursor group should be readily made into anionic or cationic groups during or typically after the polymerization reaction, by for example hydrolysis. If the polymerizable compounds comprise an anionic precursor group, the polymerization reaction herein comprises the step of forming said precursor group into an anionic group, for example by hydrolysis.

In one embodiment herein, the anionic group herein is a carboxylate group or carboxylic acid group, as defined herein. In such an embodiment, a suitable anionic precursor group for the polymerizable compound would be for example an amide or an ester group; it may be for example an ester group, such as a methyl or ethyl ester, because such ester groups are easier to hydrolyse than amide groups. Exemplary clay-crosslinked polyamide polymers are for example described in EP1160286. Exemplary clay-crosslinked polyester polymers are for example described in EP1589038. In particular when the clay-crosslinked polymers with amide or ester groups are in particulate form (particles), and are made by a process that involves forming spray-streams of droplets in a vessel, e.g. tower, said particles may be hydrolysed and dried, as described herein. This may in particular be the case for the particles described herein that have an internal void volume, e.g. having a core enclosing an internal void volume, and hence a shell of said ester-group containing clay-crosslinked polymers; hereby only the outer shell needs to be hydrolysed, which is a quick process, compared to hydrolysis of complete particles.

However, in one embodiment herein, hydrolysis is avoided, and the polymerizable compounds include or consist of compounds that have a charged group, preferably an anionic charged group, which includes, as set out herein, acids forms of such anionic groups, and/or base forms of such cationic groups.

Said clay-crosslinked superabsorbent polymers are typically made in a manner whereby said partly or substantially completely exfoliated clay dispersion and said dispersion/solution of said polymerizable compound are only combined at the spraying step or just before said spraying step, and said polymerization is only started at the spraying step or just before the spraying step, and said the polymerization commences immediately upon initiation throughout the spray-stream/droplets. Because of this, polymerization is fast and can take place before significant aggregation of the clay particles can take place. Hence, charged polymerizable compounds may be employed without the risk of significant aggregation.

The clay-crosslinked superabsorbent polymers herein may comprise "free" ions such as "free" cations such as sodium ions.

In one embodiment herein, said clay-crosslinked superabsorbent polymers herein are for example made by polymerizing polymerizible compounds, e.g. monomers, whereof at least 80% or at least 90% or even 100% by weight are polymerizable compounds, e.g. monomers, which have an anionic group (or before hydrolysis: a precursor thereof). Thus, in such an embodiment, the final polymer may comprise monomer units that do not have an anionic group, but only to a minor extend, e.g. less than about 20%, or less than 10% by weight.

For example, at least 80%, or at least 90% or even 100% of the polymerizable compounds, e.g. monomers, are compounds with a cationic and/or anionic group, preferably an anionic group.

In one embodiment, at least 80%, or at least 90% or even 100% of the polymerizable compounds, e.g. monomers, have no substituent groups other than said charged group or charged-group-precursor thereof. One charged group is an anionic group having at most two carbon atoms, or being a carboxylate group. This will provide polymers that have no hindering substituent groups and therefore a greater chain movement flexibility; this is believed to improve the greater absorption (diffusion speed) and absorption capacity.

The polymerizable compounds may be polymerizable by any type of polymerization reaction, by use of a polymerization initiator that is activated, to initiate the polymerization. In one embodiment herein, the polymerization reaction is a free radical reaction, and said polymerizable compounds, e.g. monomers, comprise therefore groups that can form chemical bonds with one another in a radical reaction. Such a free radical polymerization reaction typically takes place in the presence of a radical initiator, as described below. Particularly suitable monomers may include an unsaturated group, e.g. a C=C group.

Monomers herein include ethylene oxide; propylene oxide; ethylenimine; but typically olefinically unsaturated carboxylates and/or carboxylic acids, and/or amides or esters thereof, for example, selected acrylic acids typified by acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride; and/or any of the carboxylates of these polymerizable compounds, e.g. carboxylate salts.

In particularly suitable embodiments, the polymerizable compounds include or consist of acrylic acids and/or acrylate salts (and/or precursors thereof, such as typically acrylic esters).

Examplary anionic group precursors include methoxyethyl esters (e.g. acrylic ester), ethoxyethyl esters (e.g. acrylic ester), methyl esters (e.g. acrylic ester), and ethyl esters (e.g. acrylic ester).

It should be understood that polymerizable compounds that do not have an anionic group or precursor thereto, may be used herein. Such compounds can include, for example, monomers containing the following types of functional groups: hydroxyl groups, amino groups, and aryl groups (e.g., phenyl groups, such as those derived from styrene monomer). Other optional polymerizable monomers that may be used in addition include unsaturated hydrocarbons such as ethylene, propylene, 1-butene, butadiene, and isoprene. These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977.

The polymerisation reaction may comprise organic compounds that can provide covalent crosslinking between the polymers (so called organic covalent crosslinking agents), as known in the art, in addition to the cross-linking provided by said clay particles. This may be added as a separate dispersion or solution to the spraying step, or combined with one or more of the other dispersion(s)/solution(s) just prior to the spraying step.

The organic crosslinkers as useful herein are compounds having at least two free-radically polymerizable groups which can be free-radically interpolymerized into the polymer network. Useful crosslinkers b) are for example ethylene glycol dimethacrylate, diethylene glycol diacrylate, allyl methacrylate, trimethylolpropane triacrylate, triallylamine, tetraallyloxyethane, as described in EP-A-0 530 438, di- and triacrylates as described in EP-A-0 547 847, EP-A-0 559 476, EP-A-0 632 068, WO-A-93/21237, WO-A-03/104299, WO-A-03/104300, WO-A-03/104301 and DE-A-103 31 450, mixed acrylates which, as well as acrylate groups, comprise further ethylenically unsaturated groups, as described in DE-A-103 314 56 and prior German application 10355401.7, or crosslinker mixtures as described for example in DE-A-1 95 43 368, DE-A-1 96 46 484, WO-A-90/15830 and WO-A-02/32962.

Useful crosslinkers include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. Useful crosslinkers b) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. Advantageous crosslinkers b) include di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixed ethoxylated or propoxylated glycerol, of 3-tuply mixed ethoxylated or propoxylated trimethylolpropane, of 15-tuply ethoxylated glycerol, of 15-tuply ethoxylated trimethylolpropane, of 40-tuply ethoxylated glycerol, of 40-tuply ethoxylated trimethylolethane and also of 40-tuply ethoxylated trimethylolpropane. Crosslinkers b) may be diacrylated, dimethacrylated, triacrylated or trimethacrylated multiply ethoxylated and/or propoxylated glycerols; in particular di- and/or triacrylates of 3- to 10-tuply ethoxylated glycerol or di- or triacrylates of 1- to 5-tuply ethoxylated and/or propoxylated glycerol or triacrylates of 3- to 5-tuply ethoxylated and/or propoxylated glycerol. The organic crosslinking agent may be a hydrophilic organic crosslinking agent may also be used in herein. Examples include polyhydric alcohols such as ethylene glycol, diethylene glycol, triethylene glycol, tetraethylene glycol, polyethylene glycol, glycerol, polyglycerol, propylene glycol, diethanolamine, triethanolamine, polyoxypropylene, oxyethylene oxypropylene block copolymer, pentaerythritol and sorbitol; polyglycidyl compounds such as ethylene glycol diglycidyl ether, polyethylene glycol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether; polyvalent aziridines such as 2,2-bishydroxymethyl butanol-tris[3-(1-aziridinyl)propionate], 1,6-hexamethylenediethyleneurea and diphenylmethane-bis-4,4'-N,N'-diethyleneurea; haloepoxy compounds such as epichlorohydrin and alpha-methylchlorohydrin; polyvalent aldehydes such as glutaraldehyde and glyoxal; polyamines such as ethylenediamine, diethylenetriamine, triethylenetetramine, tetraethylenepentamine, pentaethylenehexamine and polyethyleneimine; polyisocyanates such as 2,4-toluylene diisocyanate and hexamethylene diisocyanate; polyvalent metal salts such as aluminum chloride, magnesium chloride, calcium chloride, aluminum sulfate, magnesium sulfate and calcium sulfate; and alkyl di(tri)halogenides such as 1,4-dibromobutane, 1,6-dibromohexane and 1,3,5-trichloropentane. The polyhydric alcohol, polyglycidyl compounds, polyamines and polyvalent metal salts are especially preferred.

Suitable amounts of crosslinking agent useful herein are generally between 0.005 to 5% by weight based the clay-crosslinked superabsorbent polymers, but typically low levels of for example less than 0.5% by weight, preferably less than 0.1% or less than 0.05% by weight. In one embodiment however, no such intentionally added organic covalent crosslinking agents are present during the polymerization reaction, and that the clay-crosslinked cross-linked superabsorbent polymers are free of (intentionally added) covalent organic cross-linking agents and covalent organic cross-links.

A polymerization initiator is used herein, to initiate the polymerization. This may include a so-called initiator system, comprising more than one compound to initiate the polymerization.

The initiator may need to be activated in order to initiate polymerization, or no activation may be needed. In one embodiment, the initiator is activated during the spraying step, or upon entry into the vessel, by known activation methods, including heat or radiation.

They can be appropriately selected from conventional (radical) polymerization initiators and catalysts. Materials which display good water dispersibility/solubility are preferred. Preferred may be that the polymerization reaction is a radical polymerization reaction and a radical polymerization initiator is present, selected from peroxides, hydroperoxides, hydrogen peroxide, persulfates, azo compounds and redox initiators. Useful organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-tri-methylhexanoate, acetylcyclohexylsulfonyl peroxide, dilauryl peroxide, dibenzoyl peroxide and tert-amyl perneodecanoate. Preferred azo compounds include 2,2'-azobisisobutyronitrile, 2,2'-azobis(2,4-dimethylvaleronitrile) and 2,2'-azobis(4-methoxy-2,4-dimethylvaleronitrile), especially water-soluble azo initiators, examples being 2,2'-azobis-{2-[1-(2-hydroxyethyl)-2-imidazolin-2-yl]propane}dihydrochloride,2,2'-azobis-(2-amidinopropane) dihydrochloride, 2,2'-azobis[2-(2-imidazolin-2-yl)propane]dihydrochloride and 2,2'-azobis[2-(5-methyl-2-imidazolin-2-yl)propane]dihydrochloride. Very particular preference is given to 2,2'-azobis[2-(2-imidazolin-2-yl)propane]dihydrochloride and 2,2'-azobis[2-(5-methyl-2-imidazolin-2-yl)propane]dihydrochloride.

Suitable examples include persulfates such as sodium peroxodisulfate, potassium peroxodisulfate and ammonium peroxodisulfate; hydroperoxides such as t-butyl hydroperoxide and cumene hydroperoxide; and azo compounds such as 2,2'-azobis-2-amidinopropane hydrochloride, e.g. such as VA-044, V-50 and V-501 (all manufactured by Wako Pure Chemical Industries Ltd.), and mixtures of $Fe^{2+}$; and hydrogen peroxide, or hydrogen peroxide and ascorbic acid.

The polymerization initiator may be used per se, and then it may for example be added to the carrier liquid with polymerizable monomers and/or to the clay particle dispersion; or it may be used as a dispersion or solution. It may be added just prior to the spraying step or during the spraying step. It may then be added in the form of a dispersion/solution in a carrier liquid, which is the same as the carrier liquid of the polymerizable compounds and/or of the clay particles. Examples include aqueous liquids, including water.

In one embodiment, a mixture of two or more polymerization initiators is used, for example one of the class of azo-compounds and one of the class of peroxo or peroxide compounds, as described above. This is believed to ensure fast polymerization.

In order to increase the polymerization speed, the polymerization initiator may for example be introduced onto the polymerization reaction liquid at a level of for example at least 0.1% by weight of the polymerizable compounds, or for example at least 0.3% or at least 0.5% or at least 0.7%, up to typically 10% or 5% or 3% by weight.

The polymerization rate can be controlled through the identity and amount of the initiator system used. As for example described in US2008/242817, the use of azo compound initiator or redox initiators is advantageous for directing the rate of polymerization.

For some initiators, no activation is needed; other initiators may require activation, as known in the art. The initiator may be activated by any method known in the art, including heat or radiation. Thereto, it may be desirable that the dispersions/solutions of the monomer compound and/or clay are cooled (e.g. to a temperature of less than polymerization temperature, e.g. less than 20° C., or less than 10° C.) or and/or shielded from radiation prior to introduction of the initiator, and optionally at the moment of addition of the initiator, and that said combination of initiator and dispersion/solution is exposed to the activation source, e.g. heat, radiation, only at the desired moment, for example upon introduction onto the spraying step/spraying tool or upon introduction into the vessel.

A polymerization catalyst may also be present, such as for example TMEDA, N,N,N',N'tetramethylethylenediamine.

The polymerization reaction takes place in the presence of said clay particles.

Said clay particles form bridging point between said polymers, thereby cross-linking said polymers. Typically, substantially all said polymers are bonded to at least one nano-size clay particle during said polymerization reaction, typically more than one; this may be characterized by determination of the extractable levels of said clay-crosslinked superabsorbent polymers, by the method described below. The extractable level of the clay-crosslinked superabsorbent polymers may be less than 15% (by weight of said polymers), less than 10% and even less than 5% or less than 3% of extractables.

Said clay particles in the of the superabsorbent absorbent polymer (in solid form, but also prior to the polymerization reaction herein, in the dispersion) may have a weight average largest particle dimension of less than 800 nm, less than 500, less than 300 nm, for example up to 200 nm, or up to 100 nm, or up to 70 nm or up to 60 nm or up to 40 nm; and for example a said weight average largest particle size dimension being at least 1 nm, or at least 10, or at least 20 nm. For example individual, exfoliated laponite may be used, having a weight average largest particle dimension of 30 nm. This can be determined by TEM, as described below.

Additionally or alternatively, said clay in said clay-crosslinked superabsorbent polymers are substantially all individual clay particles/platelets, and/or said clay in the dispersion is exfoliated clay of individual clay particles/platelets, as can be determined as described below.

The degree of exfoliation of the dispersion, and the related degree of aggregation (or even: absence thereof), can be determined by Cryo-TEM, as described in "Aqueous Dispersions of Silane-Functionalized Laponite Clay Platelets. A first step towards the Elaboration of Water-based Polymer/Clay Nanocomposites" Herrera et al, Langmuir 2004, 20, 1564-157.

The dispersion herein, prior to polymerization, has an exfoliation degree of at least 60%, or at least 80% or at least 90% or at least 95% or about 100%, as measurable by XRD.

The absence of aggregation in the dispersion can alternatively be determined via the percentage of individual clay particles/platelets in the final clay-crosslinked polymers herein, e.g. by use of XRD, or preferably by TEM, as described in "Polyampholytes superabsorbent nanocomposites with excellent gel strength", Kun Xu et al, ScienceDirect, Comparative Science & technology, 67 (2007), 3480-3486 (available via www.science direct.com or www.elsevier.com.)

This is done via removal of a microslice of said clay-crosslinked superabsorbent polymers, (via a ultramicrotome) and submitting this to XRD, or TEM.

In one embodiment herein, the clay in the clay-crosslinked superabsorbent polymer is in the form of individual clay particles/platelets, as measurable by TEM, as above. In one embodiment, at least 60%, at least 80% or at least 90% or even 100% of the clay are present as individual clay particles/platelets (in said clay-crosslinked polymer).

It should be understood that the particle sizes/level of individual clay particles/platelets are applicable to at least part of the clay-crosslinked superabsorbent polymers/material, but typically to the majority thereof, or all of the polymers/material. Thus the measurements above are thus done on several, at least 3, representative samples of the clay-linked superabsorbent polymers (particles), to obtain an average over said samples, which is herein referred to as the average of said polymers (particles) as a whole.

In one embodiment, the clay-crosslinked polymers are homogeneously crosslinked polymers.

Thus, the clays herein may be partially exfoliated in said dispersion; but, in certain embodiments herein the dispersion is a substantially completely (e.g. >90% by weight) or even completely exfoliated clay dispersion, e.g. at least 90% of the clay (or at least 95% or 100%) the clay being in the form of sheet-like platelets in said dispersion,—herein referred to also as "exfoliated clay dispersion".

The clay particles may be in the form of platelets, e.g. exfoliated or individual clay particles in the form of platelets, having a largest dimension and a smallest dimension, with for example a largest dimension to smallest dimension ratio of at least 2:1, or at least 10:1 or at least 25:1, up to for example 100:1.

As mentioned above, the clay particle dispersion suitable herein is typically a homogeneous dispersion of clay particles and/or it is partly or completely exfoliated clay dispersion. Exfoliation of clay is achievable by methods known in the art, e.g. by applying high shear force, either ultrasonically and/or by high shear force mixing, optionally under heating of the liquid, for example to a temperature above 40° C., or above 45° C. or above 50° C., optionally up to 70° C. or up to 60° C. or up to 55° C. For example, a Y-Tron mixer can be used for wetting the clay with the liquid, e.g. aqueous liquid or water, and keep re-circulating the dispersion for 20-30 minutes through the Y-Tron mixer for complete exfoliation. The exfoliation of the clay may also be affected by use of high-shear mixers, (such as CB Loedige mixers, Schugi mixers, Littleford mixers, Drais mixers). The tip speed of any such mixers may for example be from at least 20 $ms^{-1}$, or at least 30 $ms^{-1}$ to for example 45 or 40 or 35 $ms^{-1}$.

In particular for water-swelling clays, the clay concentration may be kept low, for example below 20% by weight of the dispersion, or less than 10% or less than 5%, but typically at least 0.5% or at least 1% by weight, or order to obtain an exfoliated dispersion.

Commercially available clays comprising a dispersant may be used herein to form an exfoliated clay dispersion in a carrier liquid, e.g. aqueous carrier liquid, including water.

The clay dispersion may thus comprise at the most very small amounts of aggregated clay, or (substantially) no aggregated clay particles, so it may be substantially free of aggregated clay. The dispersion may be filtered in order to remove aggregates. When the clay is completely exfoliated, the clay particles are present as individual clay particles, or typically platelets.

The liquid for said clay dispersion is water or a mixture of water and an organic liquid. A particularly suitable example is a liquid that is at least 80% by weight water, at least 90% or even 100% by weight water.

Examples of suitable clays herein include (water swelling) smectite, (water swelling) mica, (water swelling) hectorite, including (water swelling) laponite (synthetic laponite), (water swelling) montmorillonite, (water swelling) saponite or (water swelling) synthetic mica containing sodium as interlayer ions, kaolin, or mixtures thereof; in one embodiment, montmorillonite, hectorite, including laponite or combinations thereof.

In embodiments herein, said exfoliation of said clay is obtained in said spraying step, e.g. by use of a high shear force spray tool, e.g. nozzle(s) as are known in the art, and further described herein. Then even a non-exfoliated clay dispersion, or a partially exfoliated clay dispersion is introduced in said spraying step, and the clay is further or completely exfoliated therein by said nozzle.

The amount of clay present in the clay-crosslinked superabsorbent polymers may be chosen depending on for example the required resistance against deformation and absorbency required. For example from 1% or from 2% or from 10% or from 20% or from 25% to for example 70% or to 50% or to 40% by weight (of the polymers) of clay may be used.

The clay dispersion and said polymerizable compound solution or dispersion may be added to the spraying step process separately, to form a single dispersion/solution of said clay and polymerizable compounds in said spraying step/spraying tool (e.g., the clay is dispersed into a carrier liquid and said polymerizable compounds dispersed or dissolved in said same liquid). Alternatively, the polymerizable compound and clay dispersion/solution is obtained just (seconds) before the spraying step, to reduce the contact time of the clay and the compounds prior to polymerization.

Spraying Step and Subsequent Drying Step

The spraying step uses a spraying tool to spray a spray-stream of the (combined) dispersion(s)/solution(s) into a vessel. The spray tool has an inlet of the dispersion/solution, or multiple inlets for different dispersion(s)/solution(s), that are then combined prior to leaving said spray tool trough an outlet. The tool has typically multiple outlets, to provide multiple spray-streams.

Said inlet or multitude of inlets thus typically lead, respectively, from a reservoir with a dispersion/solution as described above, or multitude of such reservoirs, to said outlet(s) of the spray tool; hereby said outlet(s) form the dispersion/solution, or now combined dispersions/solutions into a spray-stream or a multitude of spray-streams (or in one embodiment herein into droplets). Said reservoir(s) may possibly be cooled and/or shielded from radiation. The reservoir may have a pump and said inlet(s) may have a valve(s) for controlling the flow of the dispersion(s)/solution (s). In addition, or alternatively, pressure may be applied to said spray tool via another pressure source to force the dispersion(s)/solution(s) through the spray tool.

The inlet(s) may comprise a tool for mixing the clay dispersion, polymeryzable (monomer) compound dispersion/solution, and/or initiator, or combination thereof. The spray tool may be temperature controlled.

Because the polymerization of the polymerizable compounds (monomers) may begin almost instantaneously upon the mixing of the initiator, the temperature of inlet may be reduced by cooling, e.g. to the temperatures specified herein. Cooling of the reservoirs, inlets etc. may be done by any means, for example be done by water bath, refrigeration coils, insulation.

The outlets(s) of the spray tool may however be heated.

Suitable spray tools are known in the art and for example described in U.S. Pat. No. 5,269,980 and US2008/242817 and WO96/40427. Suitable examples include so-called aerosol generators, which typically provide for droplet formation and droplet size control, as known in the art, capable of producing a spray-stream comprising, or in the form of, spherical and/or monodisperse droplets of the dispersion/solution(s) herein.

The spray tool may have an orifice plate with a plurality of orifices, or it may have a plurality of nozzles with each orifices, with a suitable diameter chosen to the required size of the spray-stream or droplets thereof. The spray-stream (or droplet) size may be further controlled by the pressure of the spray tool e.g. nozzles, e.g. for example this may be between 1 MPa and 10 MPa, causing the dispersion/solution(s) to be atomized into finer spray-stream/droplets.

If droplets (and subsequently: particles) are to be produced, the combined dispersion/solution in the spray tool may be vibrated, e.g. oscillated, and/or the nozzles or orifice plate may be vibrated or oscillated, to break up the spray-stream(s) into droplets (also referred to as aerosol), substantially uniformly-sized droplets, and/or mono-dispersed droplets.

The number of outlets, e.g. orifices, may be for example at least 5, or at least 10, more at least 50 and typically up to 1000 or up to 500. The diameter of the outlets, e.g. orifices, may be at least 50 μm, or at least 75 μm or at least 100 μm and typically up to 600, 800 or even 1000 μm.

As described in for example US2008/242817, a dropletizer plate may be used that comprises on its surface a coating material having a lower contact angle with regard to the dispersion/solution. Useful coating materials include, for example, fluorous polymers.

The spray-stream(s) enter a process vessel, such as a fluidized bed vessel or tower, known in the art. Said vessel may comprise an inert liquid, but typically, it comprises a gaseous atmosphere, e.g. a controlled and heated gaseous atmosphere. It may be a substantially inert atmosphere, such as nitrogen gas, that may comprise small levels of oxygen, for example less than 5% by weight or less than 3% by weight or less than 1% by weight.

Then, spraying the mixture results in the formation of spray stream (s), including in the shape of droplets as described below, which experience free flow through the gaseous atmosphere, e.g. a heated, controlled atmosphere, for a sufficient period of time to obtain a desired degree of polymerization and clay-crosslinking. The gas in the vessel may be a flowing in the direction opposite to the spraying direction, herein referred to as countercurrent or counter flowing gas stream, to ensure that the spray-stream/droplets are suspended in said gas stream for a long enough time to polymerize and clay-crosslink and to dry. The vessel may be a fluidized bed vessel or (spray) tower, with a moving gas stream; and/or for example a tower wherein the spray tool is placed in the top part and the spray-stream(s) or droplets perform a free fall downwards in said tower, and wherein the clay-crosslinked polymerized superabsorbent polymers are collected at the bottom part of the tower, e.g. in the form of blocks, optionally gel-phase blocks, or in one embodiment herein, in the form of particles. Said gas stream may for example be a counter-current flowing gas (stream). Fall times of between about 20 or 30 or 40 seconds to about 120 or to 90 or to 60 seconds are generally sufficient herein.

During the time in said vessel, the carrier liquid (s) may be (continuously) dried-off and evacuated from the atmosphere, to that the resulting clay-crosslinked superabsorbent polymers have a liquid content (including water) of less than 10% by weight, or as defined herein above. The clay-crosslinked superabsorbent polymer particles produced may thus be in the form of a dry powder. The size of the polymer particles will depend upon the pressure, temperatures, and time in the process vessel (tower) and other parameters, known in the art. The polymer particle size, shape, and density, however, will be relatively uniform when produced under similar conditions, and may be as described herein above. If spray-stream(s) that are not in the form of droplets are employed herein, the resulting product may be in the form of granules or (gel) blocks that can then be further treated, by grinding and optionally drying, to obtain the particles described herein, if desired.

The pressure of the atmosphere in the vessel may be ambient. It may however be a reduced below ambient, to speed up drying and evaporation of the carrier liquid, or it may be increased above ambient atmospheric pressure in order to produce a polymer particle of a more dense construction than is produced at below atmospheric pressure. The atmosphere in reaction chamber is heated to a temperature of from about 40° C. or 50° C. or 60° C. or 70° C., to 250° C., to 200° C. or to 150° C.

The relative humidity of the gas in the vessel may be low, in order to speed up drying, e.g. being below 30%.

The above described process of forming droplets results for example in the particles with an internal void volume, e.g. with a core with a void volume (partially hollow particles). Particles with a void volume which is from about 5%, or from 10% or from 20% or from 25%, to 70% or to 60% or to 50% or to 40%, by volume of said particle, on average.

In one embodiment herein, the clay-crosslinked superabsorbent polymers are polymers with anionic/cationic group precursors, e.g. amide or ester groups, pending from the polymer backbone, and said groups are hydrolysed to obtain the required cationic, or anionic groups. This may be done as a continuous process step, following the process above, for example by obtaining said particles and then continuously feeding said particles in a further vessel (tower) as described above, e.g. a fluidized bed vessel, and spraying a hydrolysis solution onto said particles. In particular in the case of the dropletization process, resulting in for example particles with a internal void volume (e.g. partially hollow particles), said hydrolysis of such particles can be affected relatively quickly on the surface of said particles. This is then followed by a drying step, and optionally a grinding step and optionally a sieving step, to obtain hydrolyzed clay-crosslinked superabsorbent polymer particles, as described herein.

Optionally, the process herein comprises the additional steps, prior to step b) of:

i) optionally providing solutions or dispersions of other auxiliary compounds such as modifiers, chelants and adding this to the spray step b), as separate dispersions/solutions, e.g. via a separate inlet, or by combining this with another dispersion/solution just prior to step b) (e.g. seconds, as described above).

Furthermore, it should be understood that in one embodiment herein, the clay dispersion and said polymerizable compound dispersion/solution and optionally said initiator may be premixed, e.g. via a high shear force mixer, as described herein, just prior to step b), e.g. several seconds as described herein. For example, separate dispersions/solutions may be made and kept in reservoirs, and then these separate dispersion/solutions are combined in a single reservoir, which may be cooled, and which connected to said inlet of said spray tool, whereby the residence time (average) of said dispersion/solution in said reservoir is only several seconds, e.g. less than 30 seconds or as described above.

The process may also comprise a step after step b) of introducing additional compounds into the vessel, e.g. tower, for example by spraying additional compounds onto the spray-stream. For example, surface-crosslinking compounds may thus be introduced, e.g. sprayed, typically in the form of a solution or dispersion, onto the spray-stream or onto the formed polymers/particles. This may be done in step c) or as a post treatment step e).

The optional post treatment step may also involve combining the resulting clay-crosslinked superabsorbent polymers (particles) with a coating agent, as known in the art.

Absorbent Structures

The absorbent structure of the invention may be any absorbent structure, used to absorb and retain liquids, such as urine or blood.

The absorbent structure is typically, or forms typically part of, a disposable absorbent article, such as interlabial products, sanitary napkins or panty liners; or adult incontinence products, such as pads or diapers; or baby, infant or toddler diapers, including training pants.

If the absorbent structure is part of a disposable absorbent article, then the absorbent structure of the invention is typically that part of an absorbent article which serves to store the bodily fluid, e.g. the storage layer of an absorbent article, also referred to as absorbent core. As known in the art, this may be in direct contact with an acquisition layer, or in one embodiment of the invention, it may form a unitary structure with an acquisition layer In yet another embodiment of the invention the absorbent structure is an acquisition layer for use in an absorbent article.

The absorbent structure may be a structure that consists of the superabsorbent material and that is then shaped into the required structure, or it may comprise additional components, such as those used in the art for absorbent structures.

The absorbent structure may comprise the superabsorbent material herein at any weight level or concentration. For example, the absorbent structure may also comprise one or more support or wrapping materials, such as foams, films, woven webs and/or nonwoven webs. When the absorbent structure is a storage layer of an absorbent article above, or when the absorbent structure comprises a layer that serves as storage layer, the structure or layer comprises large amounts of the superabsorbent material herein, compared to possible other components of the structure; the superabsorbent material is present at a level of more than 50% by weight of the structure, or even more than 70% by weight, or even more than 80% by weight, or even more than 90% by weight of the structure. The absorbent structure herein may comprise a structuring agent or matrix agent, such as non-absorbent fibers, and/or a thermoplastic component, such as a thermoplastic adhesive, or for example a non-absorbing fibrous thermoplastic adhesive component. The absorbent structure may comprise, alternatively or in addition, absorbent fibrous material, such as an airfelt material cellulose fibers etc., which can provide a matrix for immobilization of the superabsorbent material.

However, if the absorbent structure is a liquid storage layer or when the absorbent structure comprises one or more liquid storage layers, said liquid structure or said liquid storage layer comprises large amounts of the superabsorbent material herein and only very little or no absorbent (cellulose) fibers, e.g. less than 40% weight of the structure, or less than 20% by weight or less than 10% by or less than 5% by weight (of said structure) of said absorbent fibrous (cellulose) material; and/or more than 50% or more than 70% or more than 80% or more than 90% by weight (of the structure) of the superabsorbent material herein. The weight ratio of the superabsorbent material to any optional absorbent or non-absorbent fibers, or other matrix agents, is at least 1:1, at least 3:2 or at least 2:1, or at least 3:1 or at least 4:1.

The absorbent structure comprises at least a wrapping material, which wraps (the portion comprising) the superabsorbent material, a so-called core wrap material. In certain embodiments the core wrap material comprises a top layer and a bottom layer, the latter being furthest away from the skin of the user, whereby the core wrap material as a whole or the top layer and/or the bottom layer can be provided from for example a nonwoven material, such as spunbond, melt-blown and/or carded nonwovens. One material is a so-called SMS material, comprising a spunbonded, a melt-blown and a further spunbonded layer. Particularly suitable for use herein are permanently hydrophilic nonwovens, and in particular nonwovens with durably hydrophilic coatings. An alternative material comprises a SMMS-structure. The top layer and the bottom layer may be provided from two or more separate sheets of materials or they may be alternatively provided from a unitary sheet of material Non-woven materials are provided from synthetic fibers, such as PE, PET and PP. As the polymers used for nonwoven production are inherently hydrophobic, they are coated with hydrophilic coatings, e.g. coated with nanoparticles, as known in the art.

In certain embodiments the absorbent structure comprises: a wrapping material, the superabsorbent material described herein, and a thermoplastic material and/or an adhesive and/or a thermoplastic adhesive, which may be in the form of non-absorbing fibers.

absorbent structures can for example be made as follows:
a) providing a substrate material that can serve as a wrapping material;
b) depositing the superabsorbent material herein onto a first surface of the substrate material, (for example in a pattern comprising at least one zone which is substantially free of superabsorbent material, and the pattern comprising at least one zone comprising superabsorbent material, such that openings are formed between the separate zones with the superabsorbent material);
c) depositing a thermoplastic and/or adhesive material onto the first surface of the substrate material and the superabsorbent material, such that part of the thermoplastic/adhesive material is in direct contact with the first surface of the substrate and part of the thermoplastic/adhesive material is in direct contact with the superabsorbent material;
d) and then typically closing the above by folding the substrate material over, or by placing another substrate material over the above.

Disposable absorbent article comprising the absorbent structure of the invention are sanitary napkins, panty liners, adult incontinence products and baby or toddler or so-called infant diapers, including training pants, whereby articles which serve to absorb urine, e.g. adult incontinence products (pads and diapers), and (baby, infant, toddler) diapers, including training pants.

Some articles herein have a topsheet and a backsheet, which each have a front region, back region and crotch region, positioned therein between. The absorbent structure is typically positioned in between the topsheet and backsheet. Backsheets are vapour pervious but liquid impervious. Topsheet materials are at least partially hydrophilic; are also so-called apertured topsheets. The topsheet may include a skin care composition, e.g. a lotion.

These absorbent articles typically comprise a liquid impervious (air or water vapour pervious) backsheet, a fluid pervious topsheet joined to, or otherwise associated with the backsheet. Such articles are well known in the art and fully disclosed in various documents mentioned throughout the description.

Because the superabsorbent material herein has a very high absorbency capacity, it is possible to use only low levels of this material in the absorbent articles herein. Thus thin absorbent articles, such as adult and infant diapers, training pants, sanitary napkins comprising an absorbent structure, the articles having an average caliper (thickness) in the crotch region of less than 1.0 cm, less than 0.7 cm, less than 0.5 cm, or even less than 0.3 cm (for this purpose alone, the crotch region being defined as the central zone of the product, when laid out flat and stretched, having a dimension of 20% of the length of the article and 50% of the width of the article).

A diaper typically has a front waist band and a back waist band, whereby the front waist band and back waist band each have a first end portion and a second end portion and a middle portion located between the end portions, and whereby the end portions comprise each a fastening system, to fasten the front waist band to the rear waist band or whereby the end portions are connected to one another, and whereby the middle portion of the back waist band and/or the back region of the backsheet and/or the crotch region of the backsheet comprises a landing member, the landing member comprising second engaging elements selected from loops, hooks, slots, slits, buttons, magnets. Hooks, adhesive or cohesive second engaging elements. The engaging elements on the article, or diaper are provided with a means to ensure they are only engage able at certain moments, for example, they may be covered by a removable tab, which is removed when the engaging elements are to be engaged and may be re-closed when engagement is no longer needed, as described above.

Diapers and training pants herein have one or more sets of leg elastics and/or barrier leg cuffs, as known in the art.

Methods:

The measurements should be carried out, unless otherwise stated, at an ambient temperature of 23±2° C. and a relative humidity of 50±10%.

Water Content

The water content s referred to herein is measured by the EDANA method referred to above.

Centrifuge Retention Capacity (CRC)

Centrifuge Retention Capacity as referred to herein is determined by EDANA (European Disposables and Nonwovens Association) recommended test method No. 441.2-02 "Centrifuge retention capacity".

Extractables

The extractable fractions of the water-absorbing polymeric particles are determined in accordance with EDANA (European Disposables and Nonwovens Association) recommended test method No. 470.2-02 "Extractables".

EDANA test methods are obtainable for example at European Disposables and Nonwovens Association, Avenue Eugene Plasky 157, B-1030 Brussels, Belgium.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A Process for making clay-crosslinked superabsorbent polymers, comprising:
   a) providing a dispersion or solution of charged polymerizable compounds and clay particles in carrier liquid; and providing a polymerization initiator as a dispersion or solution in a carrier liquid;
   b) introducing said dispersion(s)/solution(s) and initiator of step a) into a spraying tool and spraying said dispersions/solutions and initiator into a vessel to obtain a spray-stream of thereof, starting thereby polymerization of said polymerizable compounds and crosslinking thereof by said clay particles;
   c) removing at least part of said carrier liquid, to obtain clay-crosslinked superabsorbent polymers in solid or gel form, whereby said clay particles have a weight average largest particle dimension of less than 800 nm and/or are individual clay particles; and whereby said particles have a core enclosing an internal void volume; wherein the process further comprises the use of a spraying tool with one or more inlets; and step a) comprises the sub-steps of i) providing a dispersion or solution of polymerizable compounds in a carrier liquid in a first reservoir; ii) separately providing a dispersion of clay particles in a carrier liquid in a second reservoir; iii) combining said dispersions/solutions of i) and ii) in said spraying tool; whereby said initiator, is added to said clay dispersion, polymerizable compound solution or dispersion or to said spray tool.

2. The process of claim 1, whereby said vessel is a spray tower, comprising a heated gaseous atmosphere.

3. The process of claim 1, whereby said spraying is done by:
   i) spraying said dispersion(s)/solution(s) and initiator through a multitude of orifices to form a multitude of spray-streams, that are subsequently dispersed into a multitude of droplets; and/or
   ii) spraying said dispersion(s)/solution(s) and initiator through a multitude of intermittently closed or oscillating orifices, and/or spraying said dispersion(s)/solution(s) and initiator as a vibrated, intermittently interrupted or oscillating spray-stream(s) through orifices, to form a multitude of droplets; whereby said orifices have a mean diameter of at least 50 microns, preferably up to 1000 microns.

4. The process of claim 1, whereby said polymerization in said stream is initiated by activation of said initiator by applying heat and/or radiation onto said stream.

5. The process of claim 1, whereby said polymerizable compounds include acrylate and/or acrylic acid and said polymers include polyacrylic acids and/or polyacrylates, preferably having sodium counter ions.

6. The process of claim 1, whereby said clay is selected from the group consisting of montmorillonite, saponite and hectorite, including laponite, and combinations thereof.

7. The process of claim 1, whereby said dispersion of clay particles is a homogeneous dispersion of exfoliated clay particles and/or said clay particles have a weight average largest particle size of from 10 to 100 nm.

8. The process of claim 1, whereby said spraying step b) involves spraying the dispersions/solutions and initiator in the form of: i) a multitude of droplets into a gas-containing vessel, or ii) a multitude of spray-streams into a gas-containing vessel, said streams being then dispersed into droplets; and whereby the process further comprises drying said clay-crosslinked superabsorbent polymer droplets to obtain particles having a weight average particle size of from 200 to 800 microns.

9. The process of claim 1, whereby said polymerization initiator is present in said dispersion/solution at level of from at least 0.3% by weight.

10. The process of claim 1, whereby said polymerizable compounds comprise acrylate salts.

11. The process of claim 1, whereby said dispersion or solution of polymerizable compounds and said dispersion of clay particles are combined less than 30 seconds prior to step b).

12. The process of claim 1, whereby said clay particles have a largest dimension to smallest dimension ratio of at least 2:1.

13. The process of claim 1, whereby step b) further comprises adding an organic covalent crosslinking agent to said dispersion(s)/solution(s) and initiator.

14. The process of claim 1, whereby in step c) or later, the clay-crosslinked superabsorbent polymers are treated with a surface-crosslinking compound.

15. The process of claim 1, further comprising step d) of hydrolyzing the clay-crosslinked superabsorbent polymers.

16. The process of claim 1, whereby said clay-crosslinked superabsorbent polymer is in an absorbent structure in a disposable absorbent article.

17. The process of claim 16, wherein said clay-crosslinked superabsorbent polymer is present at a level of more than 90% by weight of the structure.

18. The process of claim 1, wherein the charged polymerizable compounds comprise cations.

19. The process of claim 1, wherein the polymerizable compounds comprise acrylate salts and are at least 80% by weight anionic groups.

20. A Process for making clay-crosslinked superabsorbent polymers, comprising:
   a) providing a dispersion or solution of charged polymerizable compounds and clay particles in carrier liquid; and providing a polymerization initiator as a dispersion or solution in a carrier liquid;
   b) introducing said dispersion(s)/solution(s) and initiator of step a) into a spraying tool and spraying said dispersions/solutions and initiator into a vessel to obtain a spray-stream of thereof, starting thereby polymerization of said polymerizable compounds and crosslinking thereof by said clay particles;
   c) removing at least part of said carrier liquid, to obtain clay-crosslinked superabsorbent polymers in solid or gel form, whereby said clay particles have a weight average largest particle dimension of less than 800 nm and/or are individual clay particles; and whereby said particles have a core enclosing an internal void volume;
whereby said dispersion or solution of polymerizable compounds and said dispersion of clay particles are combined less than 30 seconds prior to step b).

21. The process of claim 20, whereby said vessel is a spray tower, comprising a heated gaseous atmosphere; whereby said spraying is done by:
   i) spraying said dispersion(s)/solution(s) and initiator through a multitude of orifices to form a multitude of spray-streams, that are subsequently dispersed into a multitude of droplets; and/or
   ii) spraying said dispersion(s)/solution(s) and initiator through a multitude of intermittently closed or oscillating orifices, and/or spraying said dispersion(s)/solution(s) and initiator as a vibrated, intermittently interrupted or oscillating spray-stream(s) through orifices, to form a multitude of droplets; whereby said orifices have preferably a mean diameter of at least 50 microns, preferably up to 1000 microns.

22. The process of claim 20, whereby said polymerizable compounds include acrylate and/or acrylic acid and said polymers include polyacrylic acids and/or polyacrylates, preferably having sodium counter ions.

23. The process of claim 20, whereby said dispersion of clay particles is a homogeneous dispersion of exfoliated clay particles and/or said clay particles have a weight average largest particle size of from 10 to 100 nm.

24. The process of claim 20, whereby said spraying step b) involves spraying the dispersions/solutions and initiator in the form of: i) a multitude of droplets into a gas-containing vessel, or ii) a multitude of spray-streams into a gas-containing vessel, said streams being then dispersed into droplets; and whereby the process further comprises drying said clay-crosslinked superabsorbent polymer droplets to obtain particles having a weight average particle size of from 200 to 800 microns.

25. The process of claim 20, whereby said polymerizable compounds comprise acrylate salts.

* * * * *